United States Patent [19]

Ryder et al.

[11] Patent Number: 4,716,177

[45] Date of Patent: Dec. 29, 1987

[54] TOLRESTAT FOR INHIBITION OF WEIGHT GAIN

[75] Inventors: Steven W. Ryder, St. James; David G. Shand, New York; John F. Mullane, Pelham, all of N.Y.

[73] Assignee: American Home Products Corporation, New York, N.Y.

[21] Appl. No.: 853,066

[22] Filed: Apr. 17, 1986

[51] Int. Cl.$^4$ ............................................. A61K 31/275
[52] U.S. Cl. ..................................... 514/524; 514/909
[58] Field of Search ......................................... 514/524

[56] References Cited

PUBLICATIONS

Cecil—*Textbook of Medicine*, sixteenth edition, W. B. Saunder Company, pp. 1057, 1058 and 1066 and 1069.

*Primary Examiner*—Frederick E. Waddell
*Attorney, Agent, or Firm*—John W. Routh

[57] ABSTRACT

A method is disclosed for inhibiting weight gain by administering an effective amount of tolrestat.

5 Claims, No Drawings

TOLRESTAT FOR INHIBITION OF WEIGHT GAIN

BACKGROUND OF THE INVENTION (a) Field of the Invention

This invention relates to a novel therapeutic use of N-[[5-(trifluoromethyl)-6-methoxy-1-naphthenyl]-thioxomethyl]-N-methylglycine. More specifically this invention relates to a method for inhibiting weight gain in humans.

(b) Prior Art

The active agent of this invention, N-[[5-(trifluoromethyl)-6-methoxy-1-naphthenyl]-thioxomethyl]-N-methylglycine or a therapeutically acceptable salt thereof, is disclosed in U.S. Pat. No. 4,568,693, issued Feb. 4, 1986. This active agent, hereinafter designated by its generic name tolrestat, previously has been reported to be useful in preventing or relieving diabetic complications such as cataracts, neuropathy, nephropathy and retinopathy (See U.S. Pat. No. 4,568,693). We have now found unexpectedly that tolrestat, either in its free acid form or in its therapeutically acceptable acid form, is useful for inhibiting weight gain in humans, and particularly humans suffering from diabetes mellitus.

This finding, coupled with the fact that tolrestat is a relatively safe drug, renders the method of this invention particularly useful and advantageous.

SUMMARY OF THE INVENTION

According to this invention a method is provided for inhibiting weight gain in a human in need of said treatment, which comprises administering to the human an effective amount of tolrestat, or a therapeutically acceptable salt thereof.

DETAILS OF THE INVENTION

According to the present method, tolrestat, either in its free acid form or in the therapeutically acceptable salt form, is employed as the active agent. Examples of suitable salt forms are described in U.S. Pat. No. 4,568,693 and include the sodium, potassium, magnesium triethylamine and benzylamine salt forms. A preferred salt form is the sodium salt, i.e. tolrestat sodium.

Tolrestat or a therapeutically acceptable addition salt thereof is administered to humans in need of weight stabilization, either orally or parenterally. For many reasons oral administration is preferred.

While tolrestat or a therapeutivally acceptable salt thereof can be administered alone, e.g. as a sole component of a filled capsule, it is preferred to formulate the compound in various dosage forms for oral or parenteral administration, e.g. tablets, or sterile solutions. Such formulations are described in U.S. Pat. No. 4,568,693, herein incorporated by reference in its entirety.

When utilizing tolrestat or one of it above-noted salts as agents for inhibiting weight gain, the total dose of active agent can range from 0.1 to 20 mg per kilogram of body weight per day with a preferred dosage range of from 100 to 400 milligrams per patient per day. Generally, a parenteral dose or an oral dose is administered in one to four applications per day. Such doses are considered to be an effective amount when, following their administration, the weight of the patient is stabilized or when the subjective symptoms complained of by said patients are reported to have been ameliorated or to have disappeared.

The effectiveness of tolrestat or its therapeutically acceptable salts as agents for inhibiting weight gain in a human has been demonstrated in human clinical trials. In a 52-week double-blind clinical trial with 550 diabetic patients, minor but statistically significant increases from baseline in body weight occurred in both the placebo and tolrestat groups. There was a statistically significant lower mean increase from baseline in body weight at the week 42 visit among the patients receiving 220 milligrams q.d. tolrestat ($+0.21 \pm 0.51$ kg) compared with the increase in body weight in the placebo group ($1.75 \pm 0.51$ kg). At other visits, although not achieving statistical significance, there was a trend for a lower increase in body weight among the tolrestat 200 mg q.d. group compared with the placebo group.

In the above 52-week double-blind clinical trial, 1 of 107 or 1% of patients receiving 200 milligrams q.d. of tolrestat, who did not report weight gain during pretreatment, experienced a weight increase compared with 10 of 104 or 10% of patients receiving placebo who did not report weight gain during pretreatment (statistically significant).

In another double-blind clinical trial lasting 8 weeks, 2 of 76 or 3% of diabetic patients receiving 400 milligrams q.d. of tolrestat who did not report weight gain during pretreatment experienced a weight increase compared with 12 of 84 or 14% of diabetic patients receiving placebo who did not report weight gain during pretreatment (statistically significant).

The method of this invention is particularly beneficial for inhibiting weight gain in a diabetic patient suffering from diabetes mellitus.

We claim:

1. A method for inhibiting weight gain in a diabetic human in need of treatment for weight stabilization which comprises administering to the diabetic human an effective amount of tolrestat or a therapeutically acceptable salt thereof.

2. The method of claim 1 in which the effective amount of tolrestat is within the range of from 0.1 to 20 mg per kilogram of body weight.

3. The method of claim 1 in which the effective amount of tolrestat is within the range of from 100 to 400 milligrams per day.

4. The method of claim 1 in which the therapeutically acceptable salt is the sodium salt.

5. The method of claim 1 in which the human being treated suffers from diabetes mellitus.

* * * * *